US006785358B2

(12) United States Patent
Johnson et al.

(10) Patent No.: US 6,785,358 B2
(45) Date of Patent: Aug. 31, 2004

(54) VOICE ACTIVATED DIAGNOSTIC IMAGING CONTROL USER INTERFACE

(75) Inventors: Mark A. Johnson, Crete, NE (US); Maureen L. Chase, Holden, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/973,560

(22) Filed: Oct. 9, 2001

(65) Prior Publication Data

US 2003/0068011 A1 Apr. 10, 2003

(51) Int. Cl.[7] ................................................. H05G 1/54
(52) U.S. Cl. ........................ 378/115; 378/98; 378/116
(58) Field of Search ............................. 378/62, 98, 115, 378/116

(56) References Cited

U.S. PATENT DOCUMENTS

| 4,641,292 A | | 2/1987 | Tunnell et al. |
| 4,776,016 A | | 10/1988 | Hansen |
| 4,807,273 A | * | 2/1989 | Haendle ..................... 378/197 |
| 5,199,080 A | | 3/1993 | Kimura et al. |
| 5,230,023 A | | 7/1993 | Nakano |
| 5,231,651 A | * | 7/1993 | Ozaki et al. ................... 378/4 |
| 5,303,148 A | * | 4/1994 | Mattson et al. ............. 600/437 |
| 5,440,606 A | * | 8/1995 | Faul et al. .................... 378/98 |
| 5,544,654 A | | 8/1996 | Murphy et al. |
| 5,970,457 A | | 10/1999 | Brant et al. |
| 6,038,534 A | | 3/2000 | Richards |
| 6,047,257 A | | 4/2000 | Dewaele |

* cited by examiner

Primary Examiner—Edward J. Glick
Assistant Examiner—Courtney Thomas
(74) Attorney, Agent, or Firm—Armstrong Teasdale LLP

(57) ABSTRACT

A X-ray exam system includes an x-ray source, a detector positioned to receive x-rays transmitted for the x-ray source, a patient table positioned so that the x-ray source emits x-rays towards a patient thereon, a video monitor for displaying images while performing an exam, and a voice activated control system coupled to the x-ray source, the detector, and the video monitor. The voice activated control system configured to control playback imaging sequencing based on a voice command to facilitate analysis of a plurality of acquired images. The control system includes an audio microphone configured to be positioned for receiving audio input from an operator, and an audio signal processor coupled to the microphone for processing amplified audio signals from the amplifier. The processing includes at least one of word and phrase recognition.

6 Claims, 2 Drawing Sheets

VOICE ACTIVATED DIAGNOSTIC IMAGING CONTROL USER INTERFACE

BACKGROUND OF THE INVENTION

This invention relates generally to medical imaging, and more particularly, to voice activated controls for use in connection with medical imaging systems.

Known medical diagnostic imaging systems require an operator (e.g., a technologist, surgeon, cardiologist) to control operation of sophisticated systems (e.g., X-ray system, computed tomography system, magnetic resonance system) as well as tend to needs of a patient. As diagnostic imaging systems and associated procedures become more sophisticated, the operator directs increased attention to the configuration and control of the imaging system and auxiliary equipment (e.g., tables, injectors, patient monitors).

In addition, interventional procedures can now be performed on a patient while performing a medical imaging procedure. Specifically, when performing an interventional procedure, an area of interest can be actively imaged. In such interventional procedures, a primary operator may use assistants to help control the imaging system, while focusing primary attention on the interventional procedure.

User interfaces used in diagnostic imaging, however, have limited mobility and accessibility. For example, typical user interfaces consist of knobs, buttons, switches and displays mounted in a specific location, or the interface range of motion is limited by electrical cables.

Remote user interfaces, such as infrared handheld remote units, are used in medical imaging. The remote user interfaces provide an operator with freedom to position the interface at a convenient location. The remote user interface, however, can be difficult to initially locate in an examination room, and may be lost during a procedure or after the procedure during clean-up. For example, the remote unit could easily be wrapped up and discarded or laundered with the sterile drapes used to cover equipment and the patient during the procedure.

User interfaces may also be obstructed by sterile drapes and covers which are placed over the equipment during a procedure. For example, an operator typically accesses the user interface through the sterile drapes, and navigates among the knobs and switches on the interface by touch. This limited accessibility requires that the operator spend more time navigating the controls without actually seeing the user interface.

Many vascular exam suites include a control room adjacent to an exam room with a window between the rooms, and possibly an intercom system for oral communication. A technologist typically remains in the control room to operate certain controls, many of which replicate controls in the exam room. The controls in the control room are typically a subset of those in the exam room. Controls that motorize equipment or turn X-ray sources on or off are located only in the exam room for safety and regulatory reasons. To avoid reaching for a control during an exam, the exam room operator may request the control room operator to perform a required task.

BRIEF SUMMARY OF THE INVENTION

In one aspect, a medical examination suite is provided. The suite comprises an exam room having a microphone and at least a portion of a medical imaging system therein. A microphone sensitivity zone is located in the exam room. The suite may further comprise a control room adjacent the exam room and having a video monitor and controls for the imaging system therein, and an equipment room having a processor, e.g., a computer therein. The computer is coupled, e.g., via video processing and display equipment, to the microphone and to the video monitor and controls for the imaging system.

In another aspect, a voice activated control subsystem for a medical imaging system is provided. The control subsystem comprises an audio microphone configured to be positioned for receiving audio input from an operator, an audio amplifier for receiving audio signals generated by the microphone, and an audio signal processor coupled to the amplifier for processing amplified audio signals from the amplifier. The processing comprising word recognition.

In yet another aspect, an X-ray exam system is provided. The X-ray exam system comprises an X-ray source, a detector positioned to receive X-rays transmitted from the X-ray source and a patient table positioned so that the X-ray source emits x-rays towards a patient thereon. The system further comprises a video monitor for displaying images while performing an exam, and a voice activated control system coupled to the X-ray source, the detector, and the video monitor. The control system comprises an audio microphone configured to be positioned for receiving audio input from an operator, and an audio signal processor coupled to the microphone for processing amplified audio signals from the amplifier. The processing comprises word recognition. The control system is coupled to controls for at least one of the X-ray source, the detector, and the monitor for executing commands received by the control system.

DETAILED DESCRIPTION OF THE INVENTION

A voice activated user interface to control diagnostic imaging equipment is described herein. Rather than navigate a series of buttons, switches, and joysticks, an operator can speak a designated command for a desired operation. In addition, the operator can obtain feedback from the system through computer-generated speech. For example, the operator can request previous X-ray exposure parameters (kV, mAs), and the system then communicates these numbers, via an audio signal, back to the operator without the operator having to consult the local display of these numbers.

Although the interface is described herein in the context of an X-ray system, the interface is not limited to practice with X-ray systems and can be utilized in many different imaging modalities. For example, the interface can be used in connection with computed tomography, magnetic resonance, positron emission tomography, ultrasound, and other imaging modalities.

The interface, in an example embodiment, is based on voice activation to control non-safety related functions of diagnostic imaging equipment. Operations controlled by voice activation include playback of imaging sequences, preparation of the imaging system for a new or different imaging sequence, analysis of acquired images, and selection of menu items from a control screen With the voice activated user interface, an operator speaks an appropriate command or sequence of commands. Therefore, the operator's hands are free to perform interventional procedures or other tasks relating to the imaging procedure. In addition, demands on the control room technologist and the amount of communication between the exam room and control room are reduced as compared to traditional interface methodologies as described above. Further, the example system described below does not require "training" in order to recognize commands from a particular operator. The term training refers to a process by which a processor adapts processing to recognize speech patterns of a particular operator and matches the patterns for that operator to particular commands. Training can be time consuming and tedious, and avoiding a need for training enhances the user friendliness of the system.

Although non-safety related functions are described as being performed by the voice recognition interface, and provided that sufficiently high accuracy levels are achieved, safety related functions also can be performed using such interface. The level of accuracy which would be sufficient for performing such safety related functions can be defined by, for example, the industry standard and regulatory agencies. Safety-critical operations include moving motorized equipment, moving the patient table, and producing X-rays that are often required to have special manual interlocks (e.g. "dead-man" or "enable" switch) by industry standards or regulatory agencies.

Figure 1:
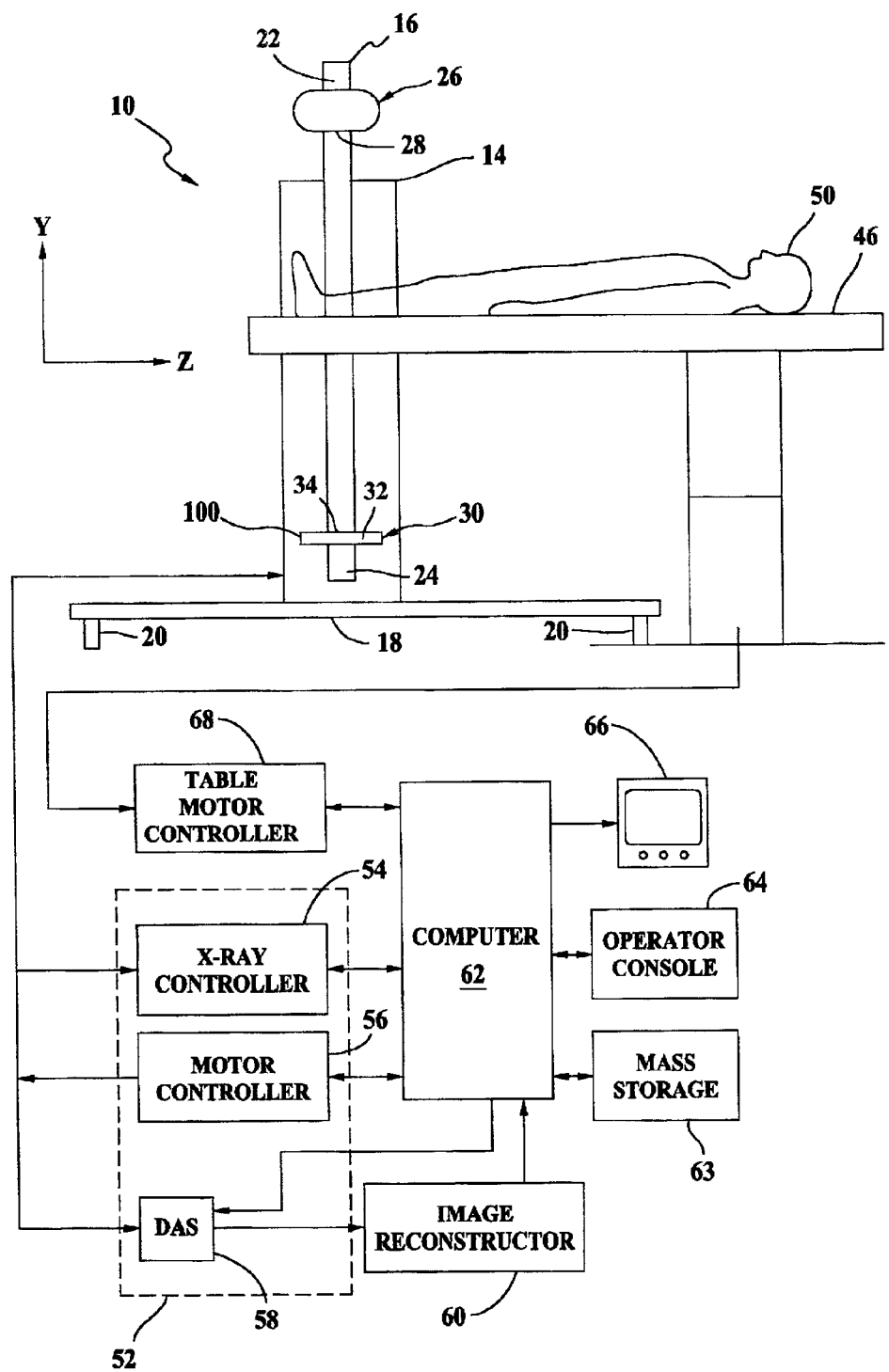
FIG. 1 is schematic illustration of an X-ray imaging system.

Set forth below is a description of one type of X-ray imaging system 10. System 10 is described herein as an example only, as explained above. More specifically, and referring to FIG. 1, imaging system 10 is shown as including a base 14 and a positioning arm 16. Base 14 extends from a portable platform 18 having a plurality of wheels 20 so that base 14 is movable relative to an object or patient 50 to be imaged. Rather than wheels, other position altering devices can be utilized, such as a pivot that allows arm 16 to tilt and rotate.

Arm 16 includes a first end portion 22 and a second end portion 24. More specifically, arm 16 rotates relative to base 14 about an axis of rotation and moves relative to base 14 to alter the respective distances between arm first end portion 22 and base 14 and arm second end portion 24 and base 14. An x-ray source assembly 26 is movably coupled to arm first end portion 22. X-ray source assembly 26 includes an X-ray source 28 configured to emit x-rays.

A detector assembly 30 is movably coupled to arm second end portion 24. Detector assembly 30 includes a detector 32 and is configured to receive the X-rays from source 28 to generate an image of the object. By moving arm 16 relative to base 14, the position of source assembly 26 may be altered so that source assembly 26 is moved toward or away from table 46. Altering the position of source assembly 26, alters the position of detector assembly 30 relative to base 14 in an opposite direction.

Detector 32, in one embodiment, is formed by a plurality of detector elements 34 which together sense the projected x-rays that pass through the object to collect image data. In the example embodiment, detector 32 is a flat panel, an image intensifier, or film. In one embodiment, detector 32 is a solid state detector or radiation imager comprising a large flat panel imaging device having a plurality of pixels 34 arranged in rows and columns. Detector 32, of course, need not be a digital detector such as a flat panel detector and could be one of many different types of known detectors.

Regarding detector 32, each pixel 34 includes a photosensor (not shown), such as a photodiode, that is coupled via a switching transistor (not shown) to two separate address lines, a scan line and a data line. In each row of pixels, each respective switching transistor (typically a thin film field effect transistor (FET)) is coupled to a common scan line through that transistor's gate electrode. In each column of pixels, the readout electrode of the transistor (e.g., the source electrode of the FET) is coupled to a data line, which in turn is selectively coupled to a readout amplifier.

During nominal operation, X-ray beams passing through patient 50 are incident on imaging array 32. The radiation is incident on a scintillator material and the pixel photosensors measure (by way of change in the charge across the diode) the amount of light generated by X-ray interaction with the scintillator. As a result, each detector element, or pixel, 34 produces an electrical signal that represents the intensity of an impinging X-ray beam and hence the attenuation of beam 16 as it passes through the object. During a scan to acquire X-ray projection data in one mode defined as a CT volume rotation mode, detector assembly 30 and source assembly 26 are rotated about the object.

System 10 also includes a table 46 for supporting patient 50. To generate an image of patient 50, arm 16 is rotated so that source assembly 26 and detector assembly 30 rotate about patient 50. More specifically, arm 16 is rotatably coupled to base 14 so that detector 32 and source 28 are rotated about object 50.

Movement of arm 16 and the operation of X-ray source assembly 26 and detector assembly 30 are governed by a control mechanism 52 of system 10. Controller, or control mechanism, 52 includes an X-ray controller 54 that provides power and timing signals to x-ray source 28 and a motor controller (motor controls) 56 that controls the position of arm 16, source assembly 26 and detector assembly 30.

A data acquisition system (DAS) 58 in control mechanism 52 samples data from detector 32 for subsequent processing. An image processor/reconstructor 60 (the term reconstructor as used herein includes reconstructors as are known in the computed tomography art, as well as processors for processing data collected in a scan (i.e., not limited to computed tomography image reconstructors)) receives sampled x-ray data from DAS 58 and performs image processing/reconstruction. The image is applied as an input to a computer 62 which stores the image in a mass storage device 63. Although not shown, a lap top computer can interface to computer 62, and images, data, and commands can be communicated between computer 62 and the lap top computer. As explained above, the voice activated interface described herein is not limited to practice with X-ray and can be utilized in connection with many other medical imaging modalities.

Computer 62 also receives commands and scanning parameters from an operator via a console 64 that has a keyboard. An associated cathode ray tube or LCD display 66 allows the operator to observe the image and other data from computer 62. The operator supplied commands and parameters are used by computer 62 to provide control signals and information to DAS 58, x-ray controller 54 and motor controller 56. Computer 62 operates a table motor controller 68 which controls position of motorized table 46 relative to system 10.

Figure 2:
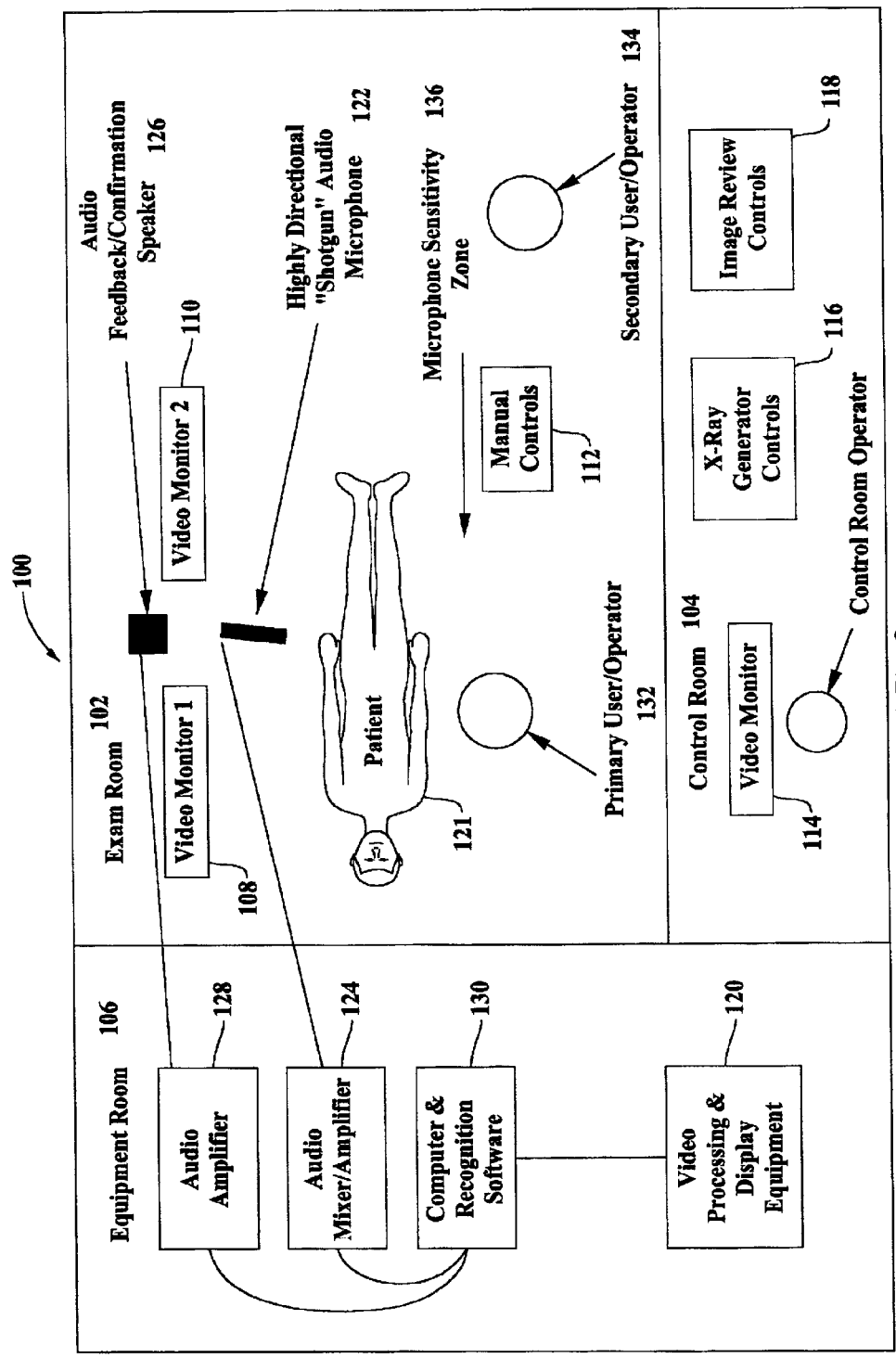
FIG. 2 is a schematic illustration of an equipment room, an exam room, and a control room for performing X-ray imaging.

FIG. 2 is a schematic illustration of an example embodiment of a vascular suite 100 including an X-ray exam room 102, a control room 104 adjacent exam room 102, and an equipment room 106. In the example embodiment, an Advantx LC+ system coupled to an Advantx DLX digital imaging subsystem, both of which are commercially available from the GE Medical Systems business of General Electric Company, Milwaukee, Wis., are utilized. Specifically, the Advantx LC+ system and the Advantx DLX subsystem include first and second video monitors 108, 110 and manual controls 112, which are located in exam room 102. The imaging system also includes a video monitor 114, X-ray generator controls 116, and image review controls 118 located in control room 104, and video and processing display equipment 120 located in equipment room 106.

The Advantx DLX subsystem typically includes an infrared remote, and the transmitter for the remote can be used anywhere within exam room 102. The infrared remote communicates with an infrared receiver in exam room 102, typically located near exam room video monitors 108 and 110. The infrared receiver in turn communicates with the DLX digital imaging subsystem using a serial (RS232) communications link. A patient 121 is shown in exam room 102 to illustrate one example embodiment of positioning of equipment in room 102.

In the example embodiment, a voice recognition subsystem includes a highly directional "shotgun" microphone 122, such as microphone model ME66/K6 commercially available from Sennheiser Electronic GmbH & Co., Am Labor 1, 30900 Wedemark, Postfach 10 02 64, 30892 Wedemark, coupled to an audio mixer/preamplifier 124 such as model SCM26S, commercially available from Shure Incorporated, 222 Hartrey Avenue, Evanston, Ill. The voice recognition subsystem further includes an audio feedback/confirmation speaker 126 coupled to an audio amplifier 128 such as model A100A, commercially available from Yamaha Pro Audio, Buena Park, Calif.

Audio amplifier 128 and audio mixer/amplifier 124 are coupled to a computer 130 including a processor, such as a Dell Lattitude Notebook with a Pentium III processor/512 MB main memory, commercially available from Dell Computer Corporation, One Dell Way, Round Rock, Tex. Although illustrated and described as being computer 130, the processing need not be performed by a computer and can be any processing device capable of performing the processing functions described below. The term computer as used herein therefore includes not only personal computer and laptop computers, but also any processor/processing device capable of performing the described processing. In addition, the processing performed by computer 130 and computer 62 could be performed by a single computer or processor and need not be separate computers/processors.

Computer 130 operates under the control of voice recognition software, such as Dragon Naturally Spealing software commercially available from Lernout & Hauspie Speech Products USA, Inc. 52 Third Avenue, Burlington, Mass. or Fonix FAAST software commercially available from Fonix Corporation, 1225 Eagle Gate Tower, 60 East South Temple, Salt Lake City, Utah. Computer 130 is coupled, via an RS232 serial interface, to video processing and display equipment 120. A standard speech application program interface (SAPI), such as the SAPI defined by Microsoft Corporation, One Microsoft Way, Redmond, Wash., is used as the interface between the control software and the voice recognition software. The SAPI facilitates use of commercially available software that conforms to the SAPI standard.

Shotgun microphone 122 allows a primary user 132 to be a considerable distance away (e.g., 4 feet), yet a secondary user 134 in exam room 102 but not located with a microphone sensitivity zone 136 will not interfere with operation of the system. Specifically, shotgun microphone 122 is insensitive to sounds and voices that are not directly in front of microphone 122, i.e., not in sensitivity zone 136. Anyone within the "sensitivity zone" 136, however, can issue a voice command.

Furthermore, shotgun microphone 122 provides the user considerable freedom to move about and remain untethered by wires, cables, or wireless "headphone-type" microphone systems. Depending on the preferences of the operator, microphone sensitivity zone 136 can be moved by repositioning microphone 122. During typical system usage, the primary operator stays near the side of patient 121 within a relatively small area. From this position, the operator can view images which appear on video monitors 108, 110, while simultaneously controlling the image processing and playback by voice commands.

The voice control subsystem recognizes a set of key words. Each key word corresponds to a command or a set of commands otherwise initiated by traditional manual controls. Upon recognition of a key word, the subsystem repeats (if enabled) the detected word to the user and executes the command. Restriction of the vocabulary to a limited number of keywords allows the use of a speaker-independent recognition system, so that no training of the speech recognition software is required.

For example, the voice recognition subsystem can be configured to recognize the following commands.

1. Cancel
2. Menu
3. Store
4. Zoom
5. Recall
6. Mask
7. Fast
8. Slow
9. Subfluoro
10. Select Plane
11. Enter
12. Sequence Plus
13. Sequence Minus
14. Prior
15. Play
16. Pause
17. Next
18. Backward
19. Forward
20. Brightness
21. Contrast
22. North
23. Up
24. South
25. Down
26. East
27. Right
28. West
29. Left
30. Northeast
31. Northwest
32. Southeast
33. Southwest
34. Pan Up
35. Pan Down
36. Pan Right
37. Pan Left
38. Calibrate Some of these commands have a one-to-one correspondence with push buttons on the infrared remote. In some cases, multiple commands are used for the same function (e.g. "Down" and "South" perform the same function, as do "Right" and "East"). Still other commands are composite functions or phrases that correspond to multiple infrared remote key presses in a specific sequence (e.g. Pan Up executes the "Up" function several times consecutively).

Generally, the computer is programmed to convert an analog audio signal from the amplifier into a digital word signal. The digital word signal is then compared (a function of the Dragon Naturally Speaking or Fonix software) with a digital list of pre-stored words. When the digital word signal from the amplifier matches a digital word on the pre-stored list, the command signal is generated that corresponds to the matched word. The command signal is communicated to the video monitor, X-ray generator controls, or image review controls in the control room, and the command is executed.

The specific embodiment described above is an example only. Different commands can be executed depending on the specific components and links selected. Further, rather than unidirectional communication, the system can be configured for bi-directional communication so that the video processing and display equipment can communicate messages on its state or errors to the voice command system. Also, the voice command system can limit or expand the choice of possible commands based on the current system state, i.e., depending on the system state fewer or more commands for execution can be made available to the operator. In addition, the voice system can be used in parallel with the manual interfaces and can be programmed so that in the event of conflicting oral and manual commands, the manual command is carried out.

While the invention has been described in terms of various specific embodiments, those skilled in the art will recognize that the invention can be practiced with modification within the spirit and scope of the claims.

What is claimed is:

1. An X-ray exam system, comprising:
   an x-ray source;
   a detector positioned to receive x-rays transmitted from said x-ray source;
   a patient table positioned so that said x-ray source emits x-rays towards a patient thereon;
   a video monitor for displaying images that are sampled and reconstructed while performing an exam; and
   a voice activated control system coupled to said x-ray source, said detector, and said video monitor, said voice activated control system for controlling playback imaging sequencing during the exam based on a voice command to facilitate analysis of a plurality of images acquired during the exam, said control system comprising an audio microphone configured to be positioned for receiving audio input from an operator, and an audio signal processor coupled to said microphone for processing amplified audio signals from said amplifier, said processing comprising at least one of word and phrase recognition, said control system coupled to controls of said x-ray source, said detector, and said monitor for executing commands received by said control system.

2. An X-ray exam system according to claim 1 further comprising an audio amplifier for receiving audio signals from said microphone, said amplifier coupled to a computer.

3. An X-ray exam system according to claim 1 wherein said microphone comprises a highly directional microphone.

4. An X-ray exam system according to claim 1 wherein said voice activated control system further comprises a speaker coupled to an audio amplifier, said audio amplifier coupled to said processor.

5. An X-ray exam system according to claim 1 wherein said X-ray source, said detector, said monitor, and said microphone are located in an exam room, a microphone sensitivity zone located in said exam room.

6. An X-ray exam system according to claim 1 wherein said controls comprise X-ray generator controls and image review controls.

* * * * *